United States Patent
Yamada et al.

(10) Patent No.: US 6,407,296 B1
(45) Date of Patent: *Jun. 18, 2002

(54) PROCESS FOR PRODUCING DIFLUOROMETHANE

(75) Inventors: Yasufu Yamada; Takashi Shibanuma; Takehide Tsuda, all of Osaka (JP)

(73) Assignee: Daikin Industries Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,746
(22) PCT Filed: Jul. 3, 1995
(86) PCT No.: PCT/JP95/01320
§ 371 (c)(1), (2), (4) Date: Dec. 23, 1996
(87) PCT Pub. No.: WO96/01241
PCT Pub. Date: Jan. 18, 1996

(30) Foreign Application Priority Data

Jul. 1, 1994 (JP) .............................................. 6-151151

(51) Int. Cl.⁷ .............................................. C07C 17/08
(52) U.S. Cl. ........................................................ 570/167
(58) Field of Search ......................................... 570/167

(56) References Cited

U.S. PATENT DOCUMENTS

| 2,005,711 A | 6/1935 | Daudt et al. | |
| 2,510,872 A | * 6/1950 | Downing | 570/167 |
| 2,749,374 A | 6/1956 | Ruh et al. | |
| 2,749,375 A | 6/1956 | Ruh et al. | |
| 4,078,007 A | 3/1978 | Ferstanding | |
| 5,495,057 A | * 2/1996 | Nam et al. | 570/167 |
| 6,291,728 B1 | * 9/2001 | Aoyama et al. | |

FOREIGN PATENT DOCUMENTS

| EP | 0 128 510 A2 | 12/1984 |
| JP | 50-106905 A | 8/1975 |
| JP | 59231030 A | 12/1984 |
| JP | 63-262487 A | 10/1988 |
| JP | 1-36556 | 8/1989 |
| JP | 7091202 B2 | 2/1990 |
| JP | 2045430 A | 5/1991 |
| JP | 4049257 A | 2/1992 |
| JP | 7-17882 A | 1/1995 |

OTHER PUBLICATIONS

The Merck Index 9th ed. p. 734, 1976.*
Feiring, A. E. *Journal of Fluorine Chemistry*, vol. 13, pp. 7–18, 1979.

* cited by examiner

*Primary Examiner*—Alan Siegel
(74) *Attorney, Agent, or Firm*—Birch, Stewart, Kolasch & Birch, LLP

(57) ABSTRACT

A process is disclosed for producing difluoromethane by fluorinating dichloromethane with hydrogen fluoride in a liquid phase in the presence of a catalyst, wherein the reaction is conducted at a temperature within the range from 80 to 150° C. under a pressure within the range from 8 to 80 kg/cm² using a mixture of antimony pentafluoride and antimony trifluoride, or antimony pentafluoride as the fluorinating catalyst. The process economically and safely produces difluoromethane from dichloromethane and hydrogen fluoride.

15 Claims, No Drawings

PROCESS FOR PRODUCING DIFLUOROMETHANE

This application is a 371 of PCT/JP95/01320 filed Jul. 3, 1995.

FIELD OF THE INVENTION

The present invention relates to a process for economically and safely producing difluoromethane, which comprises fluorinating dichloromethane with hydrogen fluoride in a liquid phase in the presence of a catalyst.

RELATED ART

Difluoromethane (hereinafter referred to as "R-32") has become a center of attention as a substitute refrigeration medium for chlorodifluoromethane which is conventionally used as a refrigeration medium for room air-conditioner.

It is known that R-32 is produced by reacting dichloromethane (hereinafter referred to as "R-30") with hydrogen fluoride (hereinafter referred to as "HF") in a gas or liquid phase in the presence of a catalyst.

U.S. Pat. Nos. 2,749,374 and 2,749,375 disclose a process wherein R-30 is reacted with HF in a liquid phase at a temperature within the range from 110 to 175° C. in the presence of an antimony chloride fluoride catalyst ($SbCl_xF_y$, x+y=3 to 5, y/(x+y)>0.8, Sb(V)>5%) to obtain R-32. In this process, however, a large amount of R-40 series compounds such as monochloromethane (hereinafter referred to as "R-40") and fluoromethane (hereinafter referred to as "R-41"), which are undesired impurities other than R-30 series compounds (R-32, R-31 and R-30), are formed as by-products. It is known that HF and antimony halide corrode the reaction apparatus and it is extremely important for the production of difluoromethane that the reaction system does not corrode the reaction apparatus. However, the above patent does not disclose that the material of a reactor shows a corrosion resistance in case of reaction under the above conditions.

Japanese Patent Kokai Publication No. 1-36556 discloses a method of adding antimony trihalide to antimony pentahalide as a method for prevention of corrosion of a vessel which is normally corroded by a mixture of HF and antimony pentahalide.

In the above Publication, there is a description that the reaction temperature is not specifically limited. However, the reaction temperature is not more than 50° C. in all Examples and Comparative Examples and a corrosion preventing effect capable of enduring practical application at more than 80° C. can not be assumed. Also, there is no description of the corrosion preventing effect for Hastelloy. There is also described that "this reaction is generally applied to a trihalomethyl compound, and is also applied to a 1,1-dihalovinyl compound which is a precursor of said compound" and the Examples do not disclose a reaction example using R-30.

Japanese Patent Kokai Publication No 59-231030 discloses a process wherein R-30 is reacted with HF in a gas phase at a reaction temperature within the range from 200 to 500° C. in the presence of an aluminum fluoride or chromium fluoride catalyst to obtain R-32. However, it can not be said that this process is an economical process from industrial points of view because the reaction temperature is high (200–500° C.) and a complicated apparatus for recovering/recycling the unreacted HF and R-30 is required.

SUMMARY OF THE INVENTION

An object of the present invention is to solve these problems in conventional techniques, thereby providing a process of economically and safely producing R-32.

An aspect of present invention resides in a process for producing difluoromethane comprising reacting dichloromethane with hydrogen fluoride in a liquid phase in the presence of a fluorinating catalyst, wherein the reaction is conducted at a temperature within the range from 80 to 150° C. under an absolute pressure within the range from 8 to 80 $kg/cm^2$ using a mixture of antimony pentafluoride and antimony trifluoride, or antimony pentafluoride having a concentration of not more than 2% by mol based on hydrogen fluoride in a liquid phase mixture, as the fluorinating catalyst.

DETAILED DESCRIPTION OF THE INVENTION

Although the cost is most cheap when R-30 is used as a starting material in the process of the present invention, chlorofluoromethane (hereinafter referred to as "R-31") can also be used. R-31 is an intermediate of the reaction wherein R-30 is reacted with HF to obtain R-32 and, therefore, only R-30 or a mixture of R-30 and R-31 may be used as the raw material. Since fluorination of R-30 and R-31 proceeds successively, it can be conducted as a series of reactions.

In the process of the present invention, a mixture of antimony pentafluoride and antimony trifluoride is used or antimony pentafluoride alone is used as the fluorinating catalyst.

When an amount of antimony trifluoride in case of using the mixture of antimony pentafluoride and antimony trifluoride as the fluorinating catalyst is decreased, the corrosion of the reactor is liable to proceed. When the amount of antimony trifluoride is increased, the reactivity is lowered. Accordingly, a molar ratio of antimony pentafluoride to antimony trifluoride, which is easily used, is normally within the range from 1:1 to 1:5. In this case, the mixture of antimony pentafluoride and antimony trifluoride in the reaction system is normally used in an amount within the range from 0.2 to 10% by mol, preferably from 2 to 8% by mol, based on HF in the liquid phase mixture. When the amount of the fluorinating agent exceeds 10% by mol, the reaction is not influenced but corrosion of the reactor becomes severe. On the other hand, when the amount is smaller than 0.2% by mol, the reaction proceeds but the formation rate of R-32 is small and the productivity per volume of the reactor is lowered.

When using only antimony pentafluoride as the fluorinating catalyst, antimony pentafluoride is normally used in an amount within the range from 0.1 to 2% by mol, preferably from 0.2 to 1% by mol, based on HF in the liquid phase mixture. When the amount is larger than 2% by mol, the corrosion of the reactor becomes severe. On the other hand, when the amount is smaller than 0.1% by mol, the formation rate of R-32 becomes small.

Antimony pentafluoride and antimony trifluoride used in the process of the present invention can be formed in situ, by fluorinating antimony chloride with a sufficient amount of HF. It is also possible to prepare antimony pentafluoride by charging antimony trifluoride or antimony trichloride, followed by chlorinating with chlorine and then fluorinating.

In the process of the present invention, HF and R-30 in a liquid or gas state are fed into a mixed liquid of HF and a fluorinating catalyst, wherein the concentration of the fluorinating catalyst has been controlled within the above range, and then R-30 is fluorinated in the liquid phase. Although the molar ratio of HF to R-30 to be fed is normally about 2:1 (stoichiometric amount), it is necessary to change the molar ratio according to the composition of the drawing gas and the composition of the recycling gas in case of recycling. It is preferred that HF is present in the liquid phase mixture in an amount of at least 5 mol per one mol of R-30. It is also possible to feed only R-30 if this value can be maintained. It is considered that a part of antimony as the catalyst is chlorinated under such a reaction condition.

The reaction temperature is preferably within the range from 80 to 150° C., more preferably from 90 to 120° C. The reaction proceeds even if the reaction temperature is lower than 80° C., but it is not suitable for practical application because the formation rate of R-32 is low and the productivity per volume of the reactor is poor. On the other hand, when the reaction temperature exceeds 150° C., the corrosion rate of the reactor is increased.

The reaction sufficiently proceeds if the charging rate to the catalyst is, for example, up to about 5 (R-30 mol/Cat. mol)/hour at 100° C.

In the process of the present invention, it is necessary to maintain the pressure conditions of the gas phase so that HF can be present in the liquid state at the above reaction temperature. For example, it is necessary to adjust the pressure to an absolute pressure of at least about 6.6 kg/cm$^2$ at 80° C. It is preferred to use the condition wherein HCl and R-32 (the reaction product) can be removed by distillation without drawing HF and R-30 (the reaction raw material). Since HCl boils at –85° C. and R-32 boils at –52° C. under the pressure of 1 atm, the reaction pressure becomes higher so that the distillation can be conducted at the more advantageous temperature, i.e. higher temperature. However, it increases the plant cost to maintain the high pressure. Accordingly, the process of the present invention is preferably conducted under the pressure of the gas phase which is an absolute pressure within the range from 8 to 60 kg/cm$^2$, more preferably from 10 to 50 kg/cm$^2$.

The process of the present invention can be conducted using a conventional apparatus which is generally known. The apparatus may be an apparatus comprising a single reactor, capable of feeding the starting material (R-30 and HF) in the liquid or gas state to the reactor and capable of heating or cooling enough to constantly maintain the reaction temperature. It is necessary that the reactor promotes contact between the reaction substances by a proper mixing method and endures the reaction pressure. It is preferred to make it possible to draw a part of the reaction mixture from a reflux condenser by providing this reactor with a reflux column and the reflux condenser. Therefore, it becomes possible to avoid entrainment of the catalyst into an effluent gas flow from the reactor and to remove HCl and R-32 as the product having comparatively low boiling point by distillation while unreacted HF and R-30 which are a substance having comparatively high boiling point and R-31 which is the intermediate product in this gas flow are remained. It is more preferred to connect the reflux column directly to the upper part of the reactor.

The material of the reactor must have a corrosion resistance enough to endure practical application under the conditions of the present invention. For example, there can be used Inconel 600, NAR25-50MTI, Hastelloy C, Hastelloy G-30, double-phase stainless steel, Hastelloy C-22 and the like. It is particularly preferred to use Hastelloy C.

The reaction mixture contains R-31 as the intermediate product and unreacted R-30 and HF, in addition to R-32 and HCl as the reaction product. These can be separated by a usual fractionation process and R-32 as the desired substance can be obtained. R-31, R-30 and HF may be used with recycling. When the unreacted substance is recycled, the molar ratio of the raw materials (HF/R-30) to be newly fed may be about 2 which is closer to a stoichiometric value. When only R-32 and HCl as the reaction product are drawn from the reflux condenser as described above, the separation of the desired substance R-32 becomes easier.

According to the preferred embodiment of the present invention, the process of the present invention is conducted by the following steps:

(1) First, a fluorinating catalyst and HF are changed in a reactor.

(2) A mixture of HF and R-30, or R-30 is added to react them. In the liquid phase mixture, HF is used in an amount that the concentration of the fluorinating catalyst is within the above range. The reaction is conducted under the above conditions to form R-32, HCl and R-31 as an intermediate product.

(3) A part or all of the reaction mixture is drawn.

(4) The drawn reaction mixture is separated by a distillation to give the desired R-32.

(5) Unreacted HF, R-30 and R-31 are optionally returned to the reactor.

The above process can be conducted by a batch process but is preferably conducted by a continuous process.

PREFERRED EMBODIMENTS OF THE INVENTION

The following Examples and Comparative Examples further illustrate the present invention in detail.

EXAMPLE 1

SbF$_3$ (35.8 g, 0.2 mol) and SbF$_5$ (21.7 g, 0.1 mol) were charged in a Hastelloy C-22 autoclave (500 ml) equipped with a stirrer, a reflux column packed with a MacMahon packing material and a reflux condenser and, after mixing, HF (250 g, 12.5 mol) was added. After heating to 100° C. with stirring, HF and R-30 were continuously fed in a rate of 1.4 mol/hour and 0.7 mol/hour, respectively. The temperature of a refrigeration medium for cooling the reflux condenser was adjusted to 5° C. so that the reaction pressure became 17 kg/cm$^2$·G, and a product was removed through the reflux condenser.

After the reaction became stable, a reflux condenser outlet gas was washed with water, washed with an alkaline, dried over calcium chloride and then analyzed by a gas chromatography (TCD).

| | |
|---|---|
| R-32 | 96.9% by mol |
| R-31 | 3.08% by mol |
| R-30 | 0.01% by mol |
| Trifluoromethane (R-23) | 15 ppm |
| R-40 | 25 ppm |

After ten hours of the reaction, the catalyst was analyzed. As a result, the following molar ratio was obtained.

SbF$_3$/SbF$_5$=2.0

EXAMPLE 2

According to the same manner as that described in Example 1 except for changing the type and amount of the catalyst to SbF$_5$ (10.8 g (0.05 mol)), the reaction was conducted.

After the reaction became stable, a reflux condenser outlet gas was washed with water, washed with an alkaline, dried over calcium chloride and then analyzed by a gas chromatography (TCD).

| R-32 | 96.4% by mol |
|------|--------------|
| R-31 | 3.56% by mol |
| R-30 | 0.02% by mol |
| R-23 | 10 ppm |
| R-40 | 20 ppm |

EXAMPLE 3

Various metal specimens for material test, wherein degreasing with acetone and measurement of the weight and size were previously conducted, a fluorinating catalyst and HF were charged in a polytetrafluoroethylene (PTFE) autoclave, and then a corrosion test was conducted under the conditions shown in Table 1. A corrosion amount was calculated by a weighing after 10 days and calculation of surface loss. The results are shown in Table 1.

TABLE 1

| Molar ratio in liquid phase mixture | | | Temperature | | Corrosion amount |
|---|---|---|---|---|---|
| HF | SbF$_5$ | SbF$_3$ | ° C. | Metal | mm/year |
| 50 | 1 | — | 80 | Inconel 600 | 8.58 |
| 50 | 1 | — | 80 | NAR 25-50 MTI | 7.21 |
| 50 | 1 | — | 80 | Hastelloy G-30 | 6.56 |
| 50 | 1 | — | 80 | Double-phase stainless steel (DP-3) | 5.16 |
| 50 | 1 | — | 80 | Hastelloy C-22 | 0.953 |
| 50 | 1 | — | 100 | Hastelloy C-22 | 1.36 |
| 60 | 1.5 | 1.5 | 100 | Hastelloy G-30 | 1.17 |
| 60 | 1.5 | 1.5 | 100 | Hastelloy C-22 | 0.669 |
| 60 | 1 | 2 | 100 | Inconel 600 | 2.33 |
| 60 | 1 | 2 | 100 | NAR 25-50 MTI | 1.56 |
| 60 | 1 | 2 | 100 | Hastelloy G-30 | 0.269 |
| 60 | 1 | 2 | 100 | Double-phase stainless steel (DP-3) | 0.744 |
| 60 | 1 | 2 | 100 | Hastelloy C-22 | 0.129 |

These results show that the corrosion is inhibited by using the process of the present invention, and also show that Hastelloy C has particularly excellent corrosion resistance in case of using these catalysts.

EXAMPLE 4

According to the same manner as that described in Example 3 except for using Hastelloy C-22 as the metal specimen for material test, adjusting the temperature to 100° C., using a mixture of SbF$_5$ and SbF$_3$ as the fluorinating catalyst and changing a molar ratio of HF to SbF$_5$ and SbF$_3$, the following corrosion tests were conducted. The results are shown in Table 2.

TABLE 2

| Molar ratio in liquid phase mixture | | | Corrosion amount |
|---|---|---|---|
| HF | SbF$_5$ | SbF$_3$ | mm/year |
| 60 | 1 | 2 | 0.129 |
| 180 | 1 | 2 | 0.027 |
| 180 | 1.2 | 1.8 | 0.139 |
| 180 | 0.75 | 2.25 | 0.004 |

The results of Table 2 show that the corrosive properties of a mixture of antimony pentafluoride and antimony trifluoride in a HF solution become smaller, as the concentration of the mixture becomes lower and the ratio of antimony trifluoride in the antimony mixture becomes higher.

EXAMPLE 5

According to the same manner as that described in Example 3 except for using Hastelloy C-22 as the metal specimen for material test, using SbF$_5$ as the fluorinating catalyst and changing a molar ratio of HF to SbF$_5$, the following corrosion tests were conducted. The results are shown in Table 3.

TABLE 3

| Molar ratio in liquid phase mixture | | Corrosion amount |
|---|---|---|
| HF | SbF$_5$ | mm/year |
| 50 | 1 | 1.36 |
| 100 | 1 | 0.554 |
| 200 | 1 | 0.168 |
| 250 | 1 | 0.069 |
| 400 | | 0.091 |

The results of Table 3 show that corrosive properties of antimony pentafluoride in a HF solution become smaller, as the concentration of antimony pentafluoride becomes lower.

EFFECT OF THE INVENTION

According to the present invention, it is possible to drastically increase a conversion rate of R-30 and HCl or a selectivity of R-32 in the reaction system, and the amount of by-products other than R-30 series compounds (R-32, R-31 and R-30) formed is very low. Typically, an amount of by-products other than R-30 series compounds formed is not more than 0.01% based on an amount of R-32 formed. Furthermore, corrosion of the material of the reactor hardly arise in the reaction using antimony pentafluoride and HF, which have high corrosive properties.

What is claimed is:

1. A process for producing difluoromethane comprising reacting dichloromethane with hydrogen fluoride in a liquid phase in the presence of a fluorinating catalyst, wherein the reaction is conducted at a temperature within the range from 80 to 150° C. under an absolute pressure within the range from 8 to 80 kg/cm$^2$ using a mixture of antimony pentafluoride and antimony trifluoride in an amount ranging from 0.2% to 10% by mol, or antimony pentafluoride in an amount ranging from 0.1% to 2% by mol based on hydrogen fluoride in a liquid phase mixture, as the fluorinating catalyst.

2. The process according to claim 1, wherein hydrogen fluoride is present in the liquid phase mixture in an amount of at least 5 mol per one mol of dichloromethane.

3. The process according to claim 1, wherein the reaction is conducted at the temperature and pressure at which hydrogen fluoride and dichloromethane remain but hydrogen chloride and difluoromethane to be formed are distilled off.

4. The process according to claim 1, wherein a reactor for conducting the reaction has a reflux column and a reflux condenser.

5. The process according to claim 1, wherein the reaction is conducted in the reactor of a material selected from the group consisting of Hastelloy C, Hastelloy G, double-phase stainless steel (DP-3) and NAR25-50MTI.

6. The process according to claim 1, which comprises the steps of:

(1) charging the fluorinating catalyst and hydrogen fluoride into a reactor;

(2) adding dichloromethane, or dichloromethane and hydrogen fluoride to the reactor to react them;

(3) removing a part or all of the reaction mixture;

(4) separating the removed reaction mixture by a distillation to give difluoromethane; and (5) optionally returning hydrogen fluoride, dichloromethane and chlorofluoromethane in the reaction mixture to the reactor.

7. The process according to claim 6, which is conducted by a continuous process.

8. The process according to claim 6, wherein difluoromethane and hydrogen chloride are removed from the reactor and hydrogen fluoride, dichloromethane and chlorofluoromethane are not removed.

9. The process according to claim 1, wherein the fluorinating catalyst is antimony pentafluoride.

10. The process according to claim 1, wherein the mixture of antimony pentafluoride and antimony trifluoride is used as the fluorinating catalyst in an amount of from 2 to 8% by mol based on hydrogen fluoride in the liquid phase mixture.

11. The process according to claim 1, wherein the fluorinating catalyst is antimony pentafluoride, and wherein the antimony pentafluoride is present in an amount of from 0.1 to 2% by mol based on hydrogen fluoride in the liquid phase mixture.

12. The process according to claim 1, wherein the fluorinating catalyst is antimony pentafluoride, and wherein the antimony pentafluoride is present in an amount of from 0.2 to 1% by mol based on hydrogen fluoride in the liquid phase mixture.

13. The process according to claim 1, wherein the reaction is conducted at a temperature within the range from 90 to 120° C.

14. The process according to claim 1, wherein the reaction is conducted under an absolute pressure within the range from 10 to 50 kg/cm$^2$.

15. The process according to claim 1, further comprising regenerating the mixture of antimony pentafluoride and antimony trifluoride or antimony pentafluoride with hydrogen flouride in the absence of added chlorine.

\* \* \* \* \*